US00PP26493P2

(12) United States Plant Patent
Koning

(10) Patent No.: US PP26,493 P2
(45) Date of Patent: Mar. 8, 2016

(54) *LAVANDULA* PLANT NAMED 'ANOUK DELUXE 179'

(50) Latin Name: *Lavandula stoechas*
Varietal Denomination: Anouk Deluxe 179

(71) Applicant: Lammert Koning, Nuis (NL)

(72) Inventor: Lammert Koning, Nuis (NL)

(73) Assignee: New Variety B.V., Kudelstaart (NL)

( * ) Notice: Subject to any disclaimer, the term of this patent is extended or adjusted under 35 U.S.C. 154(b) by 90 days.

(21) Appl. No.: 14/120,160

(22) Filed: Apr. 30, 2014

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — C. A. Whealy

(57) ABSTRACT

A new and distinct cultivar of *Lavandula* plant named 'Anouk Deluxe 179', characterized by its compact and broadly upright plant habit; freely branching growth habit; dense and bushy appearance; durable narrow leaves; freely flowering habit; violet blue and purple-colored flowers positioned on strong and erect peduncles; and good garden performance.

1 Drawing Sheet

Botanical designation: *Lavandula stoechas.*
Cultivar denomination: 'ANOUK DELUXE 179'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 179'.

The new Lavender plant is a product of a planned breeding program conducted by the Inventor in Nuis, The Netherlands. The objective of the breeding program was to develop new strong *Lavandula* plants with attractive plant form and flower coloration.

The new *Lavandula* plant originated from a cross-pollination made by the Inventor during the summer of 2008 of *Lavandula stoechas* 'Fathead', not patented, as the female, or seed, parent with a proprietary selection of *Lavandula stoechas* identified as code number 1025, not patented, as the male, or pollen, parent. The new *Lavandula* plant was discovered and selected by the Inventor during the summer of 2009 as a single flowering plant within the progeny of the stated cross-pollination in a controlled environment in Nuis, The Netherlands.

Asexual reproduction of the new *Lavandula* plant by terminal cuttings in a controlled greenhouse environment in Nuis, The Netherlands since the autumn of 2009 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 179' as a new and distinct *Lavandula* plant:

1. Compact and broadly upright plant habit.
2. Freely branching growth habit; dense and bushy appearance.
3. Durable narrow leaves.
4. Freely flowering habit.
5. Violet blue and purple-colored flowers positioned on strong and erect peduncles.
6. Good garden performance.

Plants of the new *Lavandula* differ from plants of the female parent, 'Fathead', primarily in leaf color as plants of the new *Lavandula* have darker green-colored leaves than plants of 'Fathead'. In addition, plants of the new *Lavandula* are more compact than and not as upright as plants of 'Fathead'.

Plants of the new *Lavandula* differ from plants of the male parent selection primarily in peduncle texture as peduncles of plants of the new *Lavandula* are more densely pubescent than peduncles of plants of the male parent selection.

Plants of the new *Lavandula* can be compared to plants of the *Lavandula stoechas* 'Anouk', disclosed in U.S. Plant Pat. No. 16,685. In side-by-side comparisons, plants of the new *Lavandula* differ from plants of 'Anouk' in the following characteristics:

1. Plants of the new *Lavandula* are more compact than plants of 'Anouk'.
2. Plants of the new *Lavandula* and 'Anouk' differ in leaf color.
3. Plants of the new *Lavandula* have longer flower buds than plants of 'Anouk'.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph comprises a side perspective view of a typical flowering plant of 'Anouk Deluxe 179' grown in a container.

DETAILED BOTANICAL DESCRIPTION

Plants used in the aforementioned photograph and following detailed description were grown in 2.3-liter containers during the late spring in a glass-covered greenhouse in Boskoop, The Netherlands and under cultural practices typical of commercial *Lavandula* production. Plants were pinched two times and were ten months old when the photograph and description were taken. During the production of the plants, day temperatures ranged from 14° C. to 26° C. and night temperatures ranged from 6° C. to 18° C. In the following description, color references are made to The Royal Horticultural Society Colour Chart, 2007 Edition, except where general terms of ordinary dictionary significance are used.

Botanical classification: *Lavandula stoechas* 'Anouk Deluxe 179'.

Parentage:

*Female, or seed, parent.*—*Lavandula stoechas* 'Fathead', not patented.

*Male, or pollen, parent.*—Proprietary selection of *Lavandula stoechas* identified as code number 1025, not patented.

Propagation:

*Type.*—Terminal vegetative cuttings.

*Time to initiate roots, summer.*—About one week at temperatures ranging from 14° C. to 26° C.

*Time to initiate roots, winter.*—About ten days at temperatures ranging from 14° C. to 26° C.

*Time to produce a rooted young plant, summer.*—About three to four weeks at temperatures ranging from 14° C. to 26° C.

*Time to produce a rooted young plant, winter.*—About four to six weeks at temperatures ranging from 14° C. to 26° C.

*Root description.*—Fine, fibrous; white in color.

*Rooting habit.*—Freely branching; dense.

Plant description:

*Plant and growth habit.*—Herbaceous perennial; compact and broadly upright plant habit; freely branching habit, dense and bushy appearance; moderately vigorous growth habit; flowers arranged in verticillasters on crowded spikes with showy terminal flower bracts.

*Plant height.*—About 18.5 cm.

*Plant width.*—About 28.7 cm.

*Lateral branch description.*—Quantity per plant: About 20. Length, from stem to base of inflorescence: About 8.1 cm. Diameter: About 2 mm. Internode length: About 8 mm. Strength: Strong. Aspect: Mostly upright. Texture: Densely tomentose. Color: Close to 145A to 145B; pubescence, close to 157C to 157D.

*Leaf description.*—Arrangement: Opposite, simple; sessile. Length: About 3.1 cm. Width: About 5.5 mm. Shape: Lanceolate. Apex: Acute. Base: Cuneate. Margin: Entire; revolute. Texture, upper and lower surfaces: Densely pubescent. Fragrance: Strongly aromatic, pungent. Venation pattern: Pinnate. Color: Developing leaves, upper surface: Close to 137B. Developing leaves, lower surface: Close to 138B. Fully expanded leaves, upper surface: Close to 137A to 137B; venation, close to 137B; pubescence, close to 157C to 157D. Fully expanded leaves, lower surface: Close to between 137D and 138A; venation, close to 138B; pubescence, close to 157C to 157D.

Flower description:

*Flower type, arrangement and habit.*—Small single flowers arranged in compact verticillasters on crowded spikes; freely flowering, about 250 flowers developing per inflorescence; flowers tubular with five lobes; inflorescences with showy terminal bracts.

*Natural flowering season.*—Long flowering period; continuous from late spring into the late summer in The Netherlands.

*Flower longevity on the plant.*—Individual inflorescences last about ten days on the plant; flowers not persistent.

*Fragrance.*—None detected.

*Flower buds.*—Length: About 5 mm. Diameter: About 2 mm. Shape: Oblong. Color: Close to N77A; base, close to 144C.

*Inflorescence size.*—Height: About 4.4 cm. Diameter, apex: About 2.1 cm. Diameter, base: About 1.5 cm.

*Flower size.*—Diameter: About 3 mm. Depth (height): About 8 mm.

*Petals.*—Quantity and arrangement: Five, fused into a tube. Length: About 8 mm to 9 mm. Width: About 3 mm to 3.5 mm. Shape: Roughly spatulate; lower 62.5% fused into a tube. Apex: Rounded. Margin: Entire. Texture, upper and lower surfaces: Smooth, glabrous. Color: When opening, upper and lower surfaces: Close to N92A; tube, close to N155A. Fully opened, upper and lower surfaces: Close to N92A; tube, close to N155A.

*Terminal flower bracts.*—Quantity and arrangement: About three to six positioned at inflorescence apex. Length: About 2.2 cm. Width: About 8 mm. Shape: Narrowly oblanceolate. Apex: Broadly acute. Base: Cuneate. Margin: Entire; slightly undulate. Texture, upper and lower surfaces: Smooth, glabrous. Color, upper and lower surfaces: Close to 77A to 77B; midvein, close to N79A.

*Flower bracts.*—Quantity and arrangement: Each whorl of five flowers is subtended by a single flower bract. Length: About 7 mm. Width: About 5 mm. Shape: Broadly rhomboidal. Apex: Aristate. Base: Cuneate. Margin: Entire. Texture, upper and lower surfaces: Moderately tomentose. Color, upper and lower surfaces: Close to N79C; venation, close to N79A.

*Sepals.*—Quantity and arrangement: Five, fused into a campanulate tube. Length: About 5 mm. Width: About 1 mm. Shape: Lanceolate. Apex: Acute. Margin: Entire. Texture, upper and lower surfaces: Densely tomentose. Color: When opening, upper and lower surfaces: Close to N77A; towards the base, close to 145B. Fully opened, upper and lower surfaces: Close to N77A; towards the base, close to 145C.

*Peduncles.*—Length: About 4.5 cm. Diameter: About 2 mm. Aspect: Mostly upright. Strength: Strong. Texture: Densely pubescent. Color: Close to 144B; distally, slightly tinged with close to N77C; pubescence, close to 157C to 157D.

*Reproductive organs.*—Stamens: Quantity per flower: Four. Filament length: About 1.5 mm. Anther shape:

Reniform. Anther length: About 0.5 mm. Anther color: Close to 85B to 85D. Pollen amount: Moderate. Pollen color: Close to 22A. Pistils: Quantity per flower: One. Pistil length: About 4 mm. Stigma shape: Club-shaped. Stigma color: Close to N186A. Style length: About 3.5 mm. Style color: Close to 155C. Ovary color: Close to 143B.

*Seeds and fruits.*—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7.

It is claimed:

1. A new and distinct *Lavandula* plant named 'Anouk Deluxe 179' as illustrated and described.

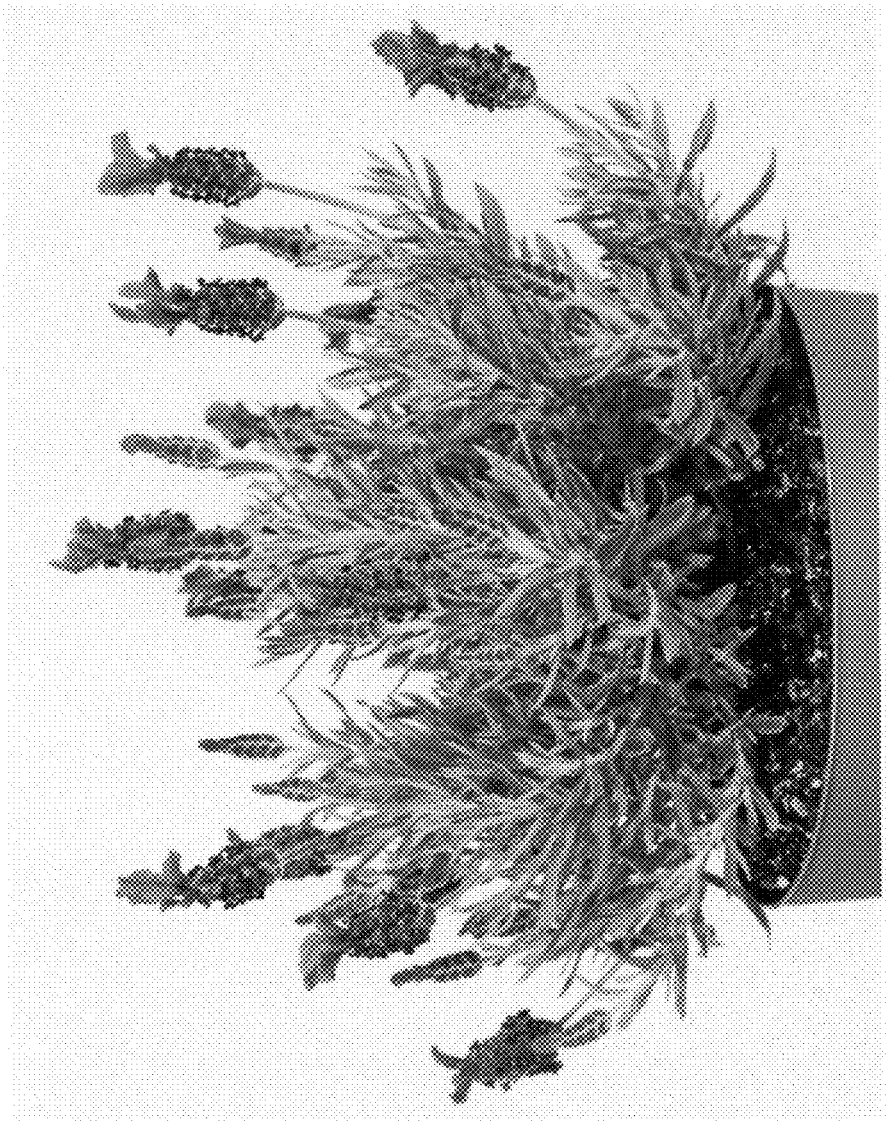

* * * * *